(12) United States Patent
Blair

(10) Patent No.: US 8,669,385 B2
(45) Date of Patent: Mar. 11, 2014

(54) OXIDATIVE CLEAVAGE OF UNSATURATED CARBOXYLIC ACIDS

(75) Inventor: Richard G. Blair, Oviedo, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 0 days.

(21) Appl. No.: 13/501,666

(22) PCT Filed: Oct. 12, 2010

(86) PCT No.: PCT/US2010/052211
§ 371 (c)(1),
(2), (4) Date: Jul. 2, 2012

(87) PCT Pub. No.: WO2011/046883
PCT Pub. Date: Apr. 21, 2011

(65) Prior Publication Data
US 2012/0264956 A1    Oct. 18, 2012

Related U.S. Application Data

(60) Provisional application No. 61/250,897, filed on Oct. 13, 2009.

(51) Int. Cl.
*C07C 51/16* (2006.01)
(52) U.S. Cl.
USPC ........................................................ 554/132

(58) Field of Classification Search
USPC ....................................................... 554/132
See application file for complete search history.

(56) References Cited

U.S. PATENT DOCUMENTS

| | | | |
|---|---|---|---|
| 4,859,799 A | 8/1989 | Campestrini et al. | |
| 5,380,931 A | 1/1995 | Srivastava et al. | |
| 5,731,460 A * | 3/1998 | Johnstone et al. | 562/408 |

OTHER PUBLICATIONS

Lee et al., Heterogeneous Permanganate Oxidations. 5. The preparation of Aldehydes by Oxidative Cleavage of Carbon-Carbon Double Bonds, J. Org. Chem., May 1993, vol. 58, pp. 2918-2919.

* cited by examiner

*Primary Examiner* — Deborah D Carr
(74) *Attorney, Agent, or Firm* — Timothy H. Van Dyke; Beusse, Wolter, Sanks, Mora & Maire, P.A.

(57) ABSTRACT

Provided are processes for the oxidative cleavage of a double bond in an unsaturated carboxylic acid. The process includes contacting the unsaturated carboxylic acid with a mild oxidizing agent and agitating the unsaturated carboxylic acid and the mild oxidizing agent for a time sufficient to cleave a double bond of the unsaturated carboxylic acid and produce a product comprising an aldehyde. The process is typically carried out in a mill, such as a ball, hammer, attrition, or jet mill.

17 Claims, 1 Drawing Sheet

100

┌─ 102
Contacting the unsaturated carboxylic acid with a mild oxidizing agent

┌─ 104
Agitating the unsaturated carboxylic acid and the mild oxidizing agent to cleave a double bond of the unsaturated carboxylic acid

100

102

Contacting the unsaturated carboxylic acid with a mild oxidizing agent

104

Agitating the unsaturated carboxylic acid and the mild oxidizing agent to cleave a double bond of the unsaturated carboxylic acid

OXIDATIVE CLEAVAGE OF UNSATURATED CARBOXYLIC ACIDS

RELATED APPLICATIONS

This application claims priority to U.S. Ser. No. 61/250,897 filed Oct. 13, 2009, which is incorporated herein by reference in its entirety.

FIELD OF THE INVENTION

The present invention relates to a process for the oxidative cleavage of double bonds, and more particularly to a process for the oxidative cleavage of double bonds in unsaturated carboxylic acids to produce aldehydes and other products.

BACKGROUND OF THE INVENTION

Oxidative cleavage of double bonds is an industrially important process for the realization of aldehydes and carboxylic acids. This cleavage is currently achieved using ozone, manganese oxides, ruthenium (IV) oxide, chromium oxides, and osmium tetroxide, and like compounds as catalysts or reagents. All of these processes, however, are extremely harsh and can lead to overoxidation of the desired product. For example, instead of aldehydes, carboxylic acids may be produced. Additionally, the catalysts can be costly, as in ruthenium compounds, or hazardous, e.g., chromium oxide, osmium tetroxide and ozone. Accordingly, there is a need for improved processes that will result in a cleaner, cost-effective process for the oxidative cleavage of double bonds.

BRIEF DESCRIPTION OF THE DRAWINGS

The invention is explained in the following description in view of the drawings that show.

DETAILED DESCRIPTION OF THE INVENTION

Figures 1, 2:
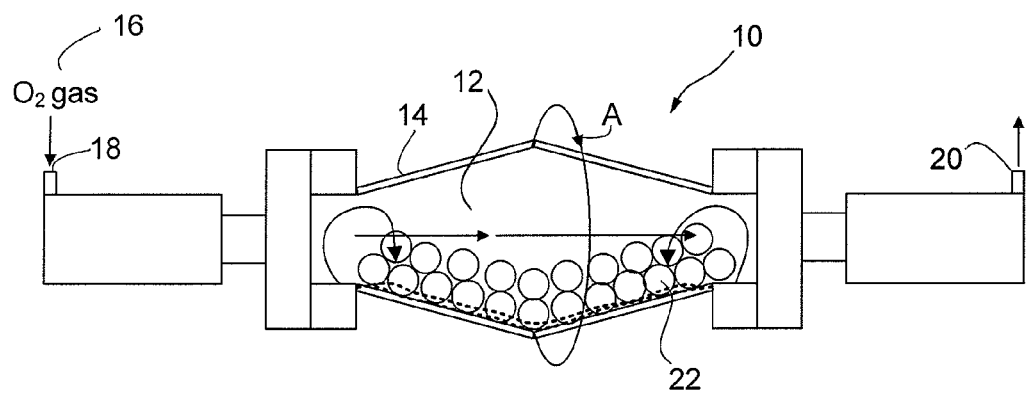
FIG. 1 depicts a schematic diagram of a process in accordance with an aspect of the present invention.
FIG. 2 depicts a mill having an air inlet and outlet in accordance with an aspect of the present invention.

The inventor has unexpectedly found that novel reaction pathways for the oxidative cleavage of double bonds can be accessed without the addition of solvents or the requirement of expensive catalysts. These pathways are otherwise not available using current synthetic techniques. In one embodiment utilizing a mechanocatalytic system, aldehydes and other useful materials can be produced when a mild oxidizing agent is combined with an unsaturated carboxylic acid, optionally along with an oxygen transfer catalyst (such as a solid catalyst), and agitated as described herein. The agitation of the unsaturated carboxylic acid in the presence of an mild oxidizing agent (e.g., air, oxygenated water, and/or hydrogen peroxide, for example, with or without an oxygen transfer catalyst), typically in a mill, provides the energy necessary to oxidatively cleave the double bond(s) of the unsaturated carboxylic acid while the oxygen transfer catalyst (if present) has a surface activity that aids in the reaction. This mechanocatalytic pathway eliminates the need for added heat and solvents to obtain the desired products.

FIG. 1 shows a schematic representation of a process 100 for the oxidative cleavage of a double bond in an unsaturated carboxylic acid. The process 100 comprises step 102 of contacting the unsaturated carboxylic acid with a mild oxidizing agent and step 104 of agitating the unsaturated carboxylic acid and the mild oxidizing agent for a time sufficient to cleave a double bond of the unsaturated carboxylic acid and to produce a product comprising an aldehyde. Typically, the process is carried out in a mill, such as one of a ball mill, an attrition mill, a hammer mill, a jet mill, or a disk mill.

The starting materials having a double bond to be cleaved by the processes described herein may be any suitable unsaturated carboxylic acid compound having at least one double bond. In a particular embodiment, the unsaturated carboxylic acid may be one or more of trans-cinnamic acid, palmitic acid, palmitoleic acid, stearic acid, oleic acid, linoleic acid, linolenic acid.

The unsaturated carboxylic acids may be provided from any suitable synthetic or naturally-occurring source. Advantageously, the processes of the present invention may be utilized to improve the properties of naturally-occurring fuel sources, such biomass-derived fuels. Biomass-derived fuels may take three forms: bio-oil, pyrolysis oil, and ethanol. Of these fuels, bio-oil and pyrolysis oil offer the potential for utilization as aviation fuels. Oils from non-food sources such as algae, castor bean, flax seed, hemp, jatropha, jojoba, neem, palm, radish, and tung offer promise for the production of fuels with kerosene-like properties. Most bio-oils consist of mixtures of unsaturated acids such as stearic acid-C18 (m.p. 69.6° C.), palmitic acid-C16 (m.p. 63-65° C.), and lauric acid-C12 (m.p. 44° C.); monounsaturated acids such as oleic acid (m.p. 13-14° C.); and polyunsaturated fatty acids such as linoleic acid (m.p. −5° C.). These acids typically have a chain length of C8-C18. The chain length and degree of saturation in these acids directly relates to the melting point, boiling point, flash point, and autoignition temperatures of these compounds. The greater the degree of saturation, the greater the melting point. The longer the chain length, the higher is the melting point. In order to improve the low temperature properties of these oils, the degree of saturation or the average acid chain length must be reduced. This is due to the fact that saturated fatty acids raise the melting point of any fuel mixture containing them. Thus, the processes of the present invention can improve the low temperature properties of these bio-oils by reducing the degree of saturation (cleaving the double bonds) of the unsaturated carboxylic acids within the bio-oils.

As an example, oleic acid can be oxidatively cleaved into nonanal (m.p. −18° C., b.p. 195° C.) and oxononanoic acid (m.p. 70° C., b.p. 181-182° C.) with oxygen, air or hydrogen peroxide. Nonanal can be utilized as is or converted to nonanol (m.p. −7° C., b.p. 215° C.) by catalytic hydrogenation. The nonanal can be distilled off and the high melting oxononanoic acid can be converted to an ester by reaction with bio-derived ethanol to produce ethyl 9-oxononanoate (m.p. 5° C.). The following represents the reaction scheme:

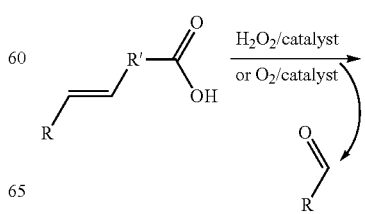

-continued

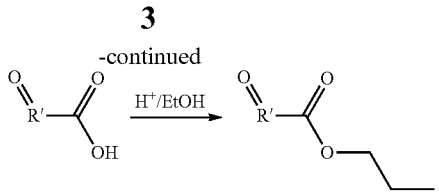

The above reaction shows the conversion of monounsaturated fatty acids (such as oleic acid, R=R'=C9) into shorter chain aldehydes and esters.

The unsaturated carboxylic acid is combined with at least a mild oxidizing agent to oxidatively cleave a double bond therein. In one embodiment, the mild oxidizing agent is an oxygen-containing component. For example, the oxygen-containing component may be one or more of air, oxygenated air, hydrogen peroxide, praseodymium oxysulfate ($Pr_2O_2SO_4$), or any other suitable oxygen-containing source, and mixtures thereof. The ratio of the unsaturated carboxylic acid to the mild oxidizing agent may be any ratio that enables a desired amount of cleavage of the double bonds of the unsaturated carboxylic acid.

As used herein, by "mild" oxidizing agent, it is meant that the oxidizing agent does not completely oxidize the double bond in the absence of agitation as described herein or in the absence of additional chemical or mechanical assistance. Put another way, as used herein, the oxidizing agent is "mild" if when the oxidizing agent is combined with an unsaturated carboxylic acid and the components are agitated together (e.g., in a mill), the reaction produces aldehydes and oxocarboxylic acids (in some cases) and the reaction substantially stops at this point. Conversely, non-mild or stronger oxidizing agents will continue the reaction further to produce carboxylic acids and dicarboxylic acids.

In another embodiment, the oxidation is facilitated by providing an oxygen-containing component and "oxygen transfer catalyst". An "oxygen transfer catalyst" is any catalyst that can reversible bind molecular oxygen from the air and shuttle it to the reaction site. In one embodiment, the oxygen transfer catalyst is a solid catalyst. By "solid," it is meant a solid material, a semi-solid material, or any other material having a water content of less than about 40% by weight. In a more specific embodiment, the solid catalyst is a solid acid material having a surface acidity. Surface acidity refers to the acidity of the solid surface of the material. Typically, surface acidity determination processes are founded on the adsorption of a base from the base's solution. The amount of base that will cover the solid surface of the solid acid material with a monolayer is defined as the surface acidity and corresponds to the $pK_a$ of the based used. The base used may be n-butylamine, cyclohexamine, or any other suitable base. The degree of surface acidity is typically expressed by the Hammet and Deyrups $H_0$ function.

$$H_0 = pK_{BH+} - \log(C_{BH+}/C_B) \quad (I)$$

Thus, in this equation, when an indicator, B, is adsorbed on an acid site of the solid surface of the material, a part of the indicator is protonated on the acid site. The strength of the acid sites may be represented by Formula (I) by the value of $pK_{BH+}$ of $BH^+$. $BH^+$ is the conjugate acid of indicator B when the concentration of $BH^+$ ($C_{BH+}$) is equal to the concentration of B ($C_B$). Therefore, the acid strength indicated by $H_0$ shows the ability of the conjugate to change into the conjugate acid by the acid sites that protonates half of the base indicator B. Under a Lewis definition, the $H_0$ value shows the ability that the electron pair can be received from half of the absorbed base indicator B. See Masuda et al., Powder Technology Handbook, 3$^{rd}$ Ed. (2006). A $H_0$ of −8.2 corresponds to an acidity of 90% sulfuric acid and a $H_0$ of −3.0 corresponds to an acidity of about 48% sulfuric acid.

Any suitable process of determining the $H_0$ of a material may be used, such as the process using the adsorption of n-butylamine from its solution in cyclohexane as set forth in *Investigation of the Surface Acidity of a Bentonite modified by Acid Activation and Thermal Treatment*, Turk. J. Chem., 2003; 27:675-681, the disclosure of which is hereby incorporated by reference in its entirety. Alternatively, indicators, generally referred to as Hammett indicators, may be used to determine the $H_0$ of a material. Hammett indicators rely on color changes that represent a particular surface acidity of the subject material.

In the present invention, a number of solid acid materials may be used. Generally, the solid acid material in the present invention may be any solid material having a surface acidity. Preferably, the solid acid material has an $H_0$ of less than about −3.0, and preferably less than about −5.6.

In one embodiment, the solid acid material is a clay material. As used herein, "a clay material" is defined as a material composed primarily of fine-grained minerals, which is generally plastic at appropriate water contents and will harden with dried or fired. Exemplary minerals that comprise the major proportion of clay materials for use in the present invention include kaolinite, halloysite, attapulgite, montmoirllonite, illite, nacrite, dickite, and anauxite. Non-limiting examples of clays for use in the present invention include fuller's earth, kaolin, and bentonite. Kaolin is a clay material that mainly consists of the mineral kaolinite. Bentonite is a clay material containing appreciable amounts of montmorillonite, and typically having some magnesium and associated therewith. Optionally, the clay material may be acid-treated to provide further surface acidity to the clay material.

In another embodiment, the solid acid material may be any aluminosilicate or hydrated aluminosilicate mineral. For example, the solid acid may be vermiculite, muscovite mica, kaolinite, halloysite, attapulgite, montmorillonite, illite, nacrite, dickite, and anauxite, or zeolites such as analcime, chabazite, heulandite, natrolite, phillipsite, and stilbite, or any mineral having the general formula $Al_2O_3 \cdot xSiO_2 \cdot nH_2O$. In a particular embodiment, the solid acid material is kaolin, which easily oxidatively cleaved double bonds within test unsaturated carboxylic acids to produce aldehydes and oxocarboxylic acids.

In another embodiment, the solid acid material may be a superacid material. Superacid materials are useful in the present invention because of the high number of acidic sites on the surface of the superacid material. Brönsted superacids may be described as acids which are stronger than 100% sulfuric acid. Lewis superacids may be described as acids that are stronger than anhydrous aluminum trichloride. Solid superacids are composed of solid media, e.g., alumina, treated with either Brönsted or Lewis acids. The solids used may include natural clays and minerals, metal oxides and sulfides, metal salts, and mixed metal oxides. Exemplary Brönsted superacids include titanium dioxide: sulfuric acid ($TiO_2:H_2SO_4$) and zirconium dioxide: sulfuric acid ($ZrO_2:H_2SO_4$) mixtures. Exemplary Lewis superacids involve the incorporation of antimony pentafluoride into metal oxides, such as silicon dioxide ($SbF_5:SiO_2$), aluminum oxide ($SbF_5:Al_2O_3$), or titanium dioxide ($SbF_5:TiO2$). In one embodiment, the solid acid is a solid superacid comprising alumina treated with 2 M sulfuric acid, filtered and calcined at about 800° C. for about 5 hours.

Alternatively, the solid acid material may be a silicate material, such as talc or any other suitable solid material having a surface acidity, such as alumina, and combinations of any of the materials described herein.

In a particular embodiment, the solid catalyst comprises a cerium-containing compound. In one embodiment, for example, the solid catalyst may be cerium-containing three-dimensional solid, such as $CeO_2$ (cerium oxide). In another embodiment, the solid catalyst comprises a layered aluminosilicate, hydrotalcite, phosphate compound, or other structure incorporating cerium. Cerium containing compounds are believed to be particularly advantageous for use in the processes of the present invention as such compounds have been shown to enable oxidative cleavage even in low energy mills, such as pebble mills.

Other examples of solid catalysts include but are not limited to layered manganese dioxide, carbon nitride, or graphite oxide. Essentially, The activity of the solid catalyst may be further enhanced by the presence of an oxygen-containing component. In one embodiment, the oxygen-containing component is one or more of air, oxygenated air, hydrogen peroxide, praseodymium oxysulfate ($Pr_2O_2SO_4$), and any other suitable oxygen-containing source. When the mild oxidizing agent comprises both a solid catalyst and an oxygen-containing component, the ratio of the solid catalyst to the oxygen-containing component may be from 1:100 to 100:1 by weight. In a particular embodiment, the ratio of the solid catalyst to the oxygen-containing component is 1:2 to 2:1 by weight. Alternatively, any other ratio of the solid catalyst to the oxygen-containing component may be utilized when effective to oxidatively cleave a double bond in an unsaturated carboxylic acid as described herein.

The resulting products of the oxidative cleavage of an unsaturated carboxylic acid typically include one or more aldehydes and one or more oxocarboxylic acids. Exemplary aldehydes include, but are not limited to, benaldehyde, nonanal, hexanal, octanal, nonanal, nonenal, 2-decanal, 2-4-decendienal, and 2-dodecanal. The aldehydes produced by the processes of the present invention disclosed herein can be used to improve the low temperature properties of bio-fuels and for the production of flavorings from bio-oils.

Oxocarboxylic acids are carboxylic acids which in addition to at least one carboxyl group as the functional group contain at least one carbonyl group, namely the aldehydo- or ketocarboxylic acids. Exemplary oxocarboxylic acids include, but are not limited to 2-oxocarboxylic acids such as glyoxylic acid, pyruvic acid or 2-oxoglutaric acid, 3-oxocarboxylic acids such as acetoacetic acid or 3-oxoglutaric acid, 4-oxocarboxylic acids such as levulinic acid, 9-oxononanoic acid, and 12-ox-dodec-9-enoic acid. The oxocarboxylic acids, 9-oxononanoic acid and 12-ox-dodec-9-enoic acid, can be obtained from plant-derived oleic and linoleic acids. The produced oxocarboxylic acids may be utilized for electrolytic hydrogen production, precursor materials for polymers, or in the production of commodity chemicals.

As noted above in step 104, the unsaturated carboxylic acid and the mild oxidizing agent are agitated for a time sufficient to provide a product comprising at least an aldehyde compound. The agitation may take place in any suitable vessel or reactor. In one embodiment, the agitating takes place in a ball, attrition, roller, jar, jet, disk, hammer, or shaker mill with a suitable milling media. The mills generally grind samples by placing them in a housing along with one or more grinding elements (milling media) and imparting motion to the housing. The housing is typically usually cylindrical and the grinding elements are typically steel balls, but may be rods, cylinders, or other shapes. Generally, the containers and grinding elements are made from the same material. An exemplary mill is a SPEX 8000D shaker mill available from SPEX CertiPrep of Metuchen, N.J. In one embodiment, the reagents may be placed in vials, e.g., 50 mL milling vials constructed of 440C stainless steel. The contents are then agitated with three 440C steel balls ½" diameter (milling media).

As the container of the relevant mill is rolled, swung, vibrated, or shaken, the inertia of the grinding elements causes the grinding elements to move independently into each other and against the container wall, agitating or grinding the sample. In one embodiment, the mill is a shaker mill using steel balls and shaking to agitate the unsaturated carboxylic acid and the mild oxidizing agent. The mills for use in the present invention may range from those having a sample capacity of a gram or less to large industrial mills with a throughput of tons per minute. Exemplary mills are available from SPEX CertiPrep of Metuchen, N.J., for example, Paul O. Abbe, Bensenville, Ill., or Union Process Inc., Akron, Ohio. For some mills, such as a steel ball mill from Paul O. Abbe, the optimal fill volume is about 25% of the total volume of the mill.

The number of steel balls required for the process is dependant upon the amount of kinetic energy available. High energy milling, typical in a shaker mill, for example, requires fewer balls than lower energy milling processes such as rolling mills. For shaking mills, a ball to sample mass ratio of about 12:1 is sufficient. For rolling mills, a ball to sample mass ratio of about 50:1 works well for a rolling rate of about 100 rpm. Lower mass ratios can be obtained by increasing the amount of kinetic energy available to the system. In a roller mill, this can be achieved through optimization of mill geometry and/or increasing the mill's rotational velocity.

A significant advantage of the present invention is that the processes described herein can be performed at ambient temperature without the need for added heat, cooling, or modifying pressure. Instead, the processes, including the agitation step, can be performed under ambient conditions. Without wishing to be bound by theory, it is believed the agitating of the reagents with the solid acid material, such as in with the aforementioned mills, provides the process with the energy required for the oxidative cleavage of the double bonds in unsaturated carboxylic acids. This is achieved though the realization of localized high pressure events during the milling process. Moreover, it is believed the agitating also allows more of the components in the mill to contact one another. For example, the agitating enables the other components within the mill (e.g., an oxygen-containing component and the unsaturated carboxylic acid) to contact the acidic sites on the surface of the solid acid material when a solid acid material is present. In another embodiment, the agitating may occur at a controlled temperature of between 5° C. and 105° C. It is contemplated that agitation may occur at any temperature degree value within this range (rounded to the nearest 0.5 centigrade unit), or within any sub-ranges within this range (rounded to the nearest 0.5 centigrade unit).

In one embodiment, the mill utilized for carrying out the processes described herein is provided with gas flow capabilities. For example, as shown in FIG. 2, there is depicted a ball mill 10 having an internal cavity 12 defined by the walls of the container 14. An oxygen-containing gas 16 can be flowed from a suitable oxygen-containing gas source into an inlet 18 of the container 14 and into the internal cavity 12. The oxygen-containing gas 16 is flowed through the internal cavity 12 and out an outlet 20. As shown, the container 14 may include the reagents (not shown) and a plurality of steel balls 22, which agitate the reagents when the container 14 is rotated in the direction shown by arrow A.

After the step of agitating 104, the reaction products may be removed with a suitable solvent, distillation, or via any suitable method known in the art. In one embodiment, when the reaction products include both aldehydes and oxocarboxylic acids, the products may be separated from one another via distillation of the lower boiling aldehydes or extraction of the mixture with water to remove the polar oxocarboxylic acids. Further, if a solid catalyst is used, the solid catalyst may be rinsed with deionized water or other suitable solvent and reused as desired.

When using a mill as described herein, the processes described herein are generally carried out as a batch process. In addition, the vessel where the agitating and oxidative cleavage takes place may be performed in a continuous attritter, which is commercially available from Union Process, Akron, Ohio. This device more generally allows the process to be carried out as a continuous process.

It is understood that the milling time can have an effect on the extent of extent of oxidative cleavage for the starting material. In one embodiment, the unsaturated carboxylic acid and the mild oxidizing agent may be agitated for a period of from 30 minutes to 10 hours.

When a solid catalyst is used, the solid catalyst may be recycled since it is not used in the reaction. Thus, optionally, the solid catalyst may be rinsed as necessary and dried to suitable level, if necessary. Thereafter, a new quantity of unsaturated carboxylic acid-containing material may be combined with the all or a portion of the recycled solid catalyst to again produce a quantity of aldehyde compounds. If no drying step is necessary, the rinsed solid acid material can be immediately reused in step 102. In either instance, the rinsed solid acid material is optionally recycled and reused to oxidatively cleave double bonds in further unsaturated carboxylic acid materials. Additional solid catalyst may be added as needed to supplement the recycled solid catalyst when reperforming step 102. Accordingly, a significant advantage of the present invention is that at least a portion of the solid catalyst may be reused continuously, thereby savings considered material and expense.

In accordance with yet another aspect of the present invention, there is provided a process for oxidative cleavage of a double bond in an unsaturated carboxylic acid. The process comprises (a) contacting the unsaturated carboxylic acid with a solid catalyst and an oxygen-containing component; and (b) agitating the unsaturated carboxylic acid and the mild oxidizing agent for a time sufficient to cleave a double bond of the unsaturated carboxylic acid and produce a product comprising an aldehyde and an oxocarboxylic acid.

The above-described processes allow for relatively benign oxygen sources (such as air and hydrogen peroxide) to be used for the production of aldehydes and oxocarboxylic acids from mono- and polyunsaturated carboxylic acids derived from plant oils, for example. The catalysts utilized are also environmentally benign and may, in some cases, be repeatedly used, thereby offering substantial cost savings.

The following examples illustrate certain embodiments of the present invention and are in no way intended to limit the scope of the invention.

EXAMPLE 1

Oxidative Cleavage of Olive Oil

Using hydrogen peroxide or air and the proper mechanocatalyst olive oil can be converted to a mixture of aldehydes and oxocarboxylic acids; 60% of the available unsaturated carboxylic acids were converted to oxidation products. In this example, 0.5 g of olive oil was mixed with 0.5 g of cerium oxide and 0.5 mL of 30% hydrogen peroxide. The reaction was placed in a 65 mL steel container with three 0.5" steel balls and agitated in a SPEX mixer mill (8000M) for 30 minutes. The reaction mixture was extracted with dichloromethane to isolate the non-polar fraction. Tables 1 and 2 give the composition of non-polar compounds produced from the oxidative cleavage of olive oil.

TABLE 1

Non-polar oxidation products produced from the mechanocatalytic cleavage of olive oil.

| Compound | Melting point (° C.) | Boiling point (° C.) | Flash point (° C.) | flavor |
|---|---|---|---|---|
| hexanal | −63 | 119-124 | 25 | green; fatty |
| octanal | −51.73 | *171* | 52 | honey; fatty; citrus; fruity apple; coconut; grape; grapefruit; lemon; lime; melon; oily; orange; waxy; nutty; fatty; citrus; peach; rose; |
| nonanal | −18 | 196.5 | 63 | vegetable; meaty; fishy |
| 2-nonenal | −45.54 | *202.64* | 84 | waxy; fatty oily; orange; citrus; floral; fatty; waxy; |
| 2-decenal | −34.27 | *221.98* | 96 | meaty; green |
| 2,4 decadienal | −39.35 | *227.75* | 98 | citrus; fatty; meaty |
| 2-dodecenal | −11.73 | *257.95* | 113 | orange; fatty; herbaceous |
| palmitic acid | 63-64 | 351-352 | 206 | |
| oleic acid | 13-14 | 360 | 113 | |

The italicized values are calculated properties.

TABLE 2

Composition of the product obtained from the oxidative cleavage of olive oil with 30% hydrogen peroxide and cerium oxide

| Compound | % yield | Parent compound |
|---|---|---|
| hexanal | 20.65 | linoleic acid |
| octanal | 2.03 | palmitoleic acid |
| nonanal | 5.47 | oleic acid |

TABLE 2-continued

Composition of the product obtained from the oxidative cleavage of olive oil with 30% hydrogen peroxide and cerium oxide

| Compound | % yield | Parent compound |
|---|---|---|
| 2-nonenal | 1.94 | linoleic acid |
| 2-decenal | 9.13 | linoleic acid |
| 2,4 decadienal | 2.13 | linolenic acid |
| 2-dodecenal | 9.32 | linoleic acid |
| Unreacted Olive Oil | 49.33 | olive oil |

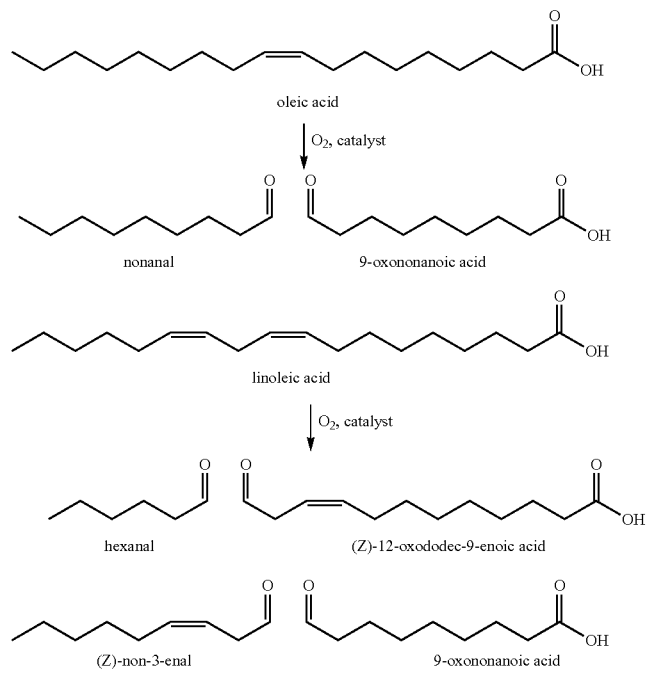

The majority of the non-polar compounds observed in the treatment of olive oil are from the oxidative cleavage of oleic and linoleic acid.

EXAMPLE 2

Trans-Cinnaminic Acid

To further investigate the ability of different reagents in oxidatively cleaving double bonds in an unsaturated carboxylic acid, e.g., trans-cinnamic acid, the reagents set forth in Table 3 below were added to a 65 mL reaction container with three 0.5" steel balls and agitated in a SPEX Certiprep 8000D ball mill. The mill was run for 30 minutes at a motor speed/rate of 1725 rpm.

TABLE 3

| Reagent 1 | Amount (g) | Reagent 2 | Amount (g) | Reagent 3 | Amount | Products |
|---|---|---|---|---|---|---|
| Trans-cinnamic acid | 0.5014 | Kaolin | 0.5016 | | | No Products |
| Trans-cinnamic acid | 1.0022 | | | | | No Products |
| Trans-cinnamic acid | 0.5033 | Kaolin | 0.5012 | Water | 20 Drops | No Products |
| Trans-cinnamic acid | 1.0011 | Water | 20 Drops | | | Benzaldehyde |
| Trans-cinnamic acid | 0.5080 | Kaolin | 0.5075 | 3% H2O2 | 20 Drops | Benzaldehyde |

TABLE 3-continued

| Reagent 1 | Amount (g) | Reagent 2 | Amount (g) | Reagent 3 | Amount | | Products |
|---|---|---|---|---|---|---|---|
| Trans-cinnamic acid | 1.0027 | 3% H2O2 | 20 Drops | | | | Benzaldehyde |
| Trans-cinnamic acid | 0.4943 | Palladium | 0.4913 | | | | No Products |
| Trans-cinnamic acid | 0.5036 | PdO | 0.5068 | | | | No Products |
| Trans-cinnamic acid | 0.5028 | CuO | 0.5028 | | | | No Products |
| Trans-cinnamic acid | 0.5016 | MnO2 | 0.5021 | | | | No Products |
| Trans-cinnamic acid | 0.5013 | MoO3 | 0.5014 | | | | No Products |
| Trans-cinnamic acid | 0.5034 | Ag2O | 0.5003 | | | | No Products |
| Trans-cinnamic acid | 0.5027 | Kaolin | 1.0006 | 30% H2O2 | 20 | Drops | Benzaldehyde |
| Trans-cinnamic acid | 1.5000 | 30% H2O2 | 20 drops | | | | Benzaldehyde |
| Trans-cinnamic acid | 0.5007 | Kaolin | 1.0014 | 30% H2O2 | 6 | drops | Benzaldehyde |
| Trans-cinnamic acid | 1.5022 | 30% H2O2 | 6 drops | | | | Benzaldehyde |
| Trans-cinnamic acid | 0.5000 | CeO2 | 0.5008 | Oxygenated Water | 25 | mL | Benzaldehyde |
| Trans-cinnamic acid | 0.5012 | CeO2 | 0.4998 | | | | No Products |
| Trans-cinnamic acid | 0.5010 | Pr2O2SO4 | 0.5009 | | | | No Products |

EXAMPLE 3

Oxidative Cleavage with Air

In this example, air was used as a mild oxidizing agent for the oxidative cleavage of trans cinnamic acid to benzaldehyde and glyoxylic acid. (a) 1 g of cerium oxide and 1 g of trans cinnamic acid were placed in a rolling ball mill with gass flow capabilities. Approximately 100 g of milling media were added in the form of 0.5" steel balls. The ball mill was run with air flowing through it at a rate of 0.5 cubic foot per minute. The ball mill was run for 12 hours at a speed/rate of 200 rpm to produce benzaldehyde.

The present invention, in various embodiments, includes components, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This process of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The invention claimed is:

1. A process for oxidative cleavage of a double bond in an unsaturated carboxylic acid comprising:
    (a) contacting the unsaturated carboxylic acid with a mild oxidizing agent; and
    (b) agitating the unsaturated carboxylic acid and the mild oxidizing agent for a time sufficient to cleave a double bond of the unsaturated carboxylic acid and produce a product comprising an aldehyde;
    wherein the mild oxidizing agent comprises an oxygen transfer catalyst comprising kaolin and an oxygen-containing component comprising at least one of hydrogen peroxide, oxygenated water, pure oxygen, or air.

2. The process of claim 1, wherein at least step (b) is carried out in a mill, wherein the mill is one of a ball mill, an attrition mill, a hammer mill, or a jet mill.

3. The process of claim 1, further comprising:
    (c) after step (b) of agitating, recovering a first solution comprising the aldehyde via recovering a first solution comprising the aldehyde via an aqueous solvent.

4. The process of claim 3, further comprising:
(e) after steps (c) and (d) of recovering, reusing at least a portion of the mild oxidizing agent and repeating at least steps (a) and (b).

5. The process of claim 1, wherein the unsaturated carboxylic acid is selected from the group consisting of trans-cinnamic acid, palmitic acid, palmitoleic acid, stearic acid, oleic acid, linoleic acid, linolenic acid, and combinations thereof.

6. The process of claim 1, wherein the mild oxidizing agent comprises at least one of air, oxygenated air, hydrogen peroxide, praseodymium oxysulfate, or mixtures thereof.

7. The process of claim 1, wherein the ratio of kaolin to the oxygen-containing component is from 0.5:1 to 2:1 by weight.

8. The process of claim 1, wherein the oxygen transfer catalyst is a solid catalyst comprising cerium oxide.

9. The process of claim 8, wherein the ratio of cerium oxide to the oxygen containing component is from 0.5:1 to 2:1 by weight.

10. The process of claim 1, wherein the carboxylic acid is from an oil from a source selected from the group consisting of algae, castor bean, flax seed, hemp, jatropa, neem, palm, radish, and tung.

11. A process for oxidative cleavage of a double bond in an unsaturated carboxylic acid comprising:
(a) contacting the unsaturated carboxylic acid with a solid catalyst and an oxygen-containing component; and
(b) agitating the unsaturated carboxylic acid and the oxygen-containing component for a time sufficient to cleave a double bond of the unsaturated carboxylic acid and produce a product comprising an aldehyde and an oxo-carboxylic acid;
wherein (i) the solid catalyst is a layered solid acid material and the oxygen-containing component comprises at least one of hydrogen peroxide and oxygenated water, and/or wherein the solid catalyst comprises cerium oxide.

12. The process of claim 11, wherein at least step (b) is carried out in a mill, wherein the mill is one of an a ball mill, attrition mill, a hammer mill, a jet mill, or a disk mill.

13. The process of claim 11, further comprising:
(c) after step (b) of agitating, recovering a first solution comprising the aldehyde via an aqueous solvent.

14. The process of claim 13, further comprising:
(e) after step (c) of recovering, reusing at least a portion of the oxygen-containing component and repeating at least steps (a) and (b).

15. The process of claim 11, wherein the unsaturated carboxylic acid is selected from the group consisting of trans-cinnamic acid, palmitic acid, palmitoleic acid, stearic acid, oleic acid, linoleic acid, linolenic acid, and combinations thereof.

16. The process of claim 11, wherein the oxygen-containing component comprises at least one of air, oxygenated air, hydrogen peroxide, praseodymium oxysulfate, or mixtures thereof.

17. The process of claim 11, wherein during said agitating, a reaction occurs which substantially stops with the production of aldehydic compounds.

* * * * *